United States Patent [19]

Low

[11] Patent Number: 4,681,738
[45] Date of Patent: Jul. 21, 1987

[54] METHOD AND APPARATUS FOR STERILIZING OBJECTS

[76] Inventor: Sidney Low, Black Stump Rd., R.R. 1 Box 873, Weems, Va. 22576

[21] Appl. No.: 825,580

[22] Filed: Feb. 4, 1986

[51] Int. Cl.[4] ............... A01N 25/08; A01N 25/12; A61L 2/18; B08B 7/04
[52] U.S. Cl. ............... 422/28; 134/25.4; 239/54; 422/37; 424/421
[58] Field of Search ............... 422/1, 5, 28, 29, 32, 422/37, 38, 33, 41, 39; 134/7, 25.1, 25.4, 37; 239/54, 56, 60; 424/26; 604/289, 290, 19

[56] References Cited

U.S. PATENT DOCUMENTS

| | | | |
|---|---|---|---|
| 3,118,773 | 1/1964 | Bennett et al. | 422/41 |
| 3,205,620 | 9/1965 | Woodworth et al. | 134/7 |
| 3,294,099 | 12/1966 | Warthen et al. | 424/26 |
| 3,933,991 | 1/1976 | Dorn et al. | 423/522 |
| 4,108,682 | 8/1978 | Takeda et al. | 422/140 |
| 4,259,383 | 3/1981 | Eggensperger et al. | 422/37 |
| 4,334,998 | 6/1985 | Rios et al. | 422/140 |

FOREIGN PATENT DOCUMENTS 3026258 7/1980 Fed. Rep. of Germany ........ 429/26

Primary Examiner—David L. Lacey
Assistant Examiner—C. M. Delahunty
Attorney, Agent, or Firm—Bacon & Thomas

[57] ABSTRACT

A method and apparatus for sterilizing objects, particularly hands, is disclosed in which an object is immersed in an agitated bed of small, porous particles charged with a liquid disinfectant. The agitated particles strike the object and release a microscopic amount of disinfectant onto the surface of the object, thereby killing contaminating microorganisms on the object.

6 Claims, 4 Drawing Figures

METHOD AND APPARATUS FOR STERILIZING OBJECTS

BACKGROUND OF THE INVENTION

1. Technical Field of the Invention

This invention is directed to a method and apparatus for sterilizing objects, particularly hands, by dry scrubbing in an agitated bed of small, porous particles charged with a liquid disinfectant.

2. Description of the Prior Art

Recent research has proven that many infections and communicable diseases are readily spread by the human hand. Some researchers have termed this "hand to hand", but in reality it is usually "hand to object to hand". In other words, a person with soiled hands touches an object that is then contaminated with whatever pathogen(s) he had on his hand. Later, another person touches the contaminated object and transfers the pathogen(s) to his hand. Since many pathogens live outside the human body for up to five hours, the seriousness of this problem is obvious.

It has been shown that 90% of persons with the common cold carry live rhinovirus on their hands. It is, therefore, not surprising that nearly 75% of common colds are caused by "hand to hand" contact. When one also considers that 100% of the population carries *E. Coli* and 30 to 50% carries *Staph. Aureus,* the relationship between personal hygiene, "hand to hand" contact and the spread of infections and communicable diseases is evident.

Currently, there are two methods of insuring that one has sterile hands, i.e., hands free of pathogens, washing and wearing sterile gloves. Medical personnel have traditionally washed with surgical soap, i.e., soaps containing anti-bacterial agents such as hexaresorcinol. Rubber gloves are sterilized prior to use via cryoclaving, heating or other means.

Washing as the means of achieving sterilization has a number of disadvantages, including inconvenience, time, and chapping or drying of skin as well as allergic reactions to the anti-bacterial agents in the soap. Research has shown that even medical personnel in an acute care hospital are not conscientious about hand cleanliness. Many nurses have 15 to 200 patient contacts between hand washings. The average medical doctor has 16 patient contacts between hand washings. The result of this lack of hand cleanliness is that 6% of all hospital patients will acquire an infection or disease while in the hospital.

Rubber gloves also have a number of disadvantages in that they are relatively expensive, hard to don, uncomfortable and tend to make hand movements awkward. A further drawback is that the gloves are only sterile if properly donned and only prior to contacting contaminated objects.

Accordingly, there remains a need in the art for a means to achieve effective sterilization of hands and other objects, which avoids the problems associated with hand washing, sterilized gloves or other conventional sterilization methods.

SUMMARY OF THE INVENTION

Accordingly, it is the primary object of the invention to provide a method and apparatus for sterilizing objects, particularly hands, which is convenient, simple, fast, effective against a wide range of pathogens and cost effective.

Another object of the invention is to provide a method and apparatus for sterilizing hands which keep the hands dry.

Other objects and advantages of the invention will be evident to those of skill in the art upon review of the complete disclosure contained herein.

The foregoing objects and advantages are achieved by a method for sterilizing an object in which the object to be sterilized is placed in an agitated bed of porous particles which have been impregnated with a liquid disinfectant such that the particles strike the object immersed therein and release a micro-thin film of the liquid disinfectant onto the surface of the object, thereby killing the pathogens on the object. The method of the invention is conducted by an apparatus which comprises a container for containing a bed of porous particles impregnated with a liquid disinfectant and means for agitating said porous particals in the container.

Further details of the invention are provided in the detailed description which follows.

BRIEF DESCRIPTION OF THE FIGURES OF DRAWING

DETAILED DESCRIPTION OF THE PREFERRED EMBODIMENTS

The invention dry scrubs a person's hands (or other object) in a violently agitated bed of small, porous, inert particles charged with an effective liquid disinfectant. Each inert, porous particle stores a relatively large quantity of the liquid disinfectant within its pores which bleeds to the outside of the particle, thereby micro-wetting its surface. The multitude of violently agitated particles scrub the person's hands, releasing the liquid disinfectant to kill pathogens and leaving a micro-film of the disinfectant on the person's hands. The term "micro" as used in this application is intended to connote dimensions on the order of fractions of microns to many microns.

A suitable disinfectant, such as an aqueous solution of stable $ClO_2$, will react with the thin film of fatty acid on a person's hand liberating microscopic amounts of $ClO_2$, further enhancing the effectiveness of the disinfectant. However, for all intents and purposes, the hand remains dry.

Figure 1:
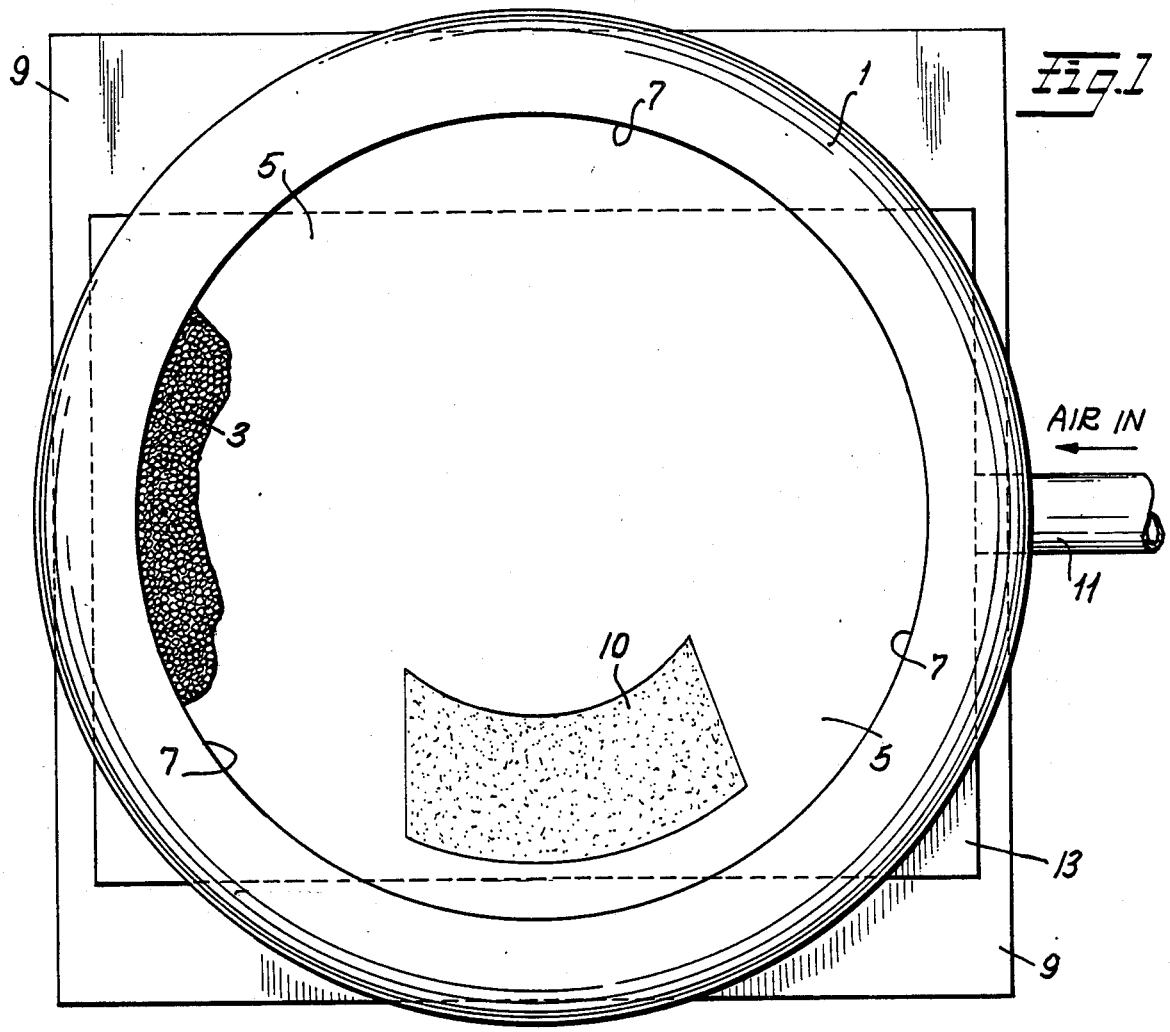
FIG. 1 shows a top view of an apparatus designed in accordance with the invention.
Figure 2:
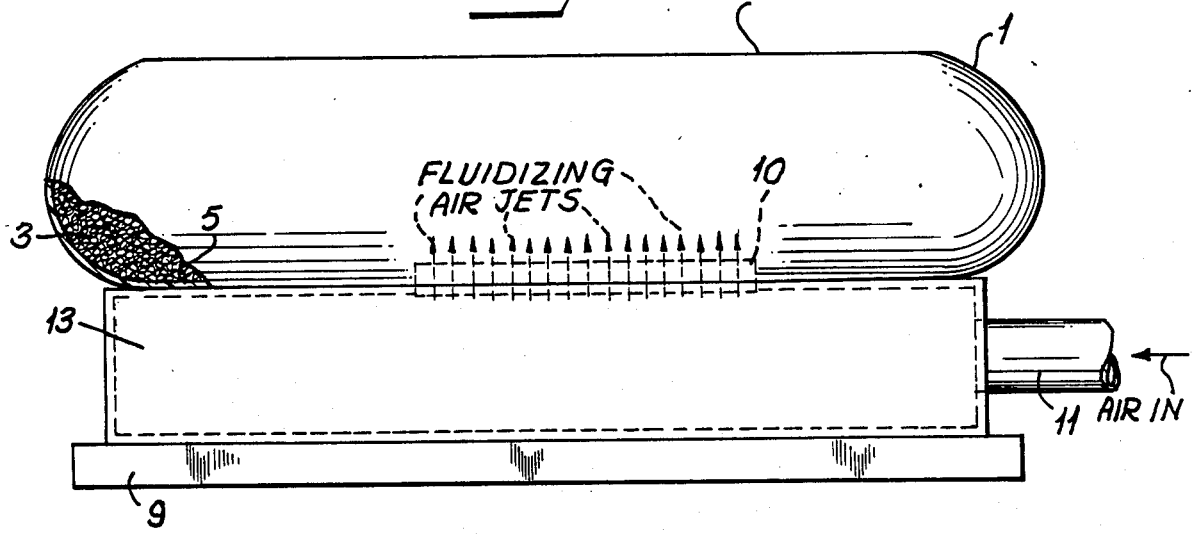
FIG. 2 shows a side view in partial cross section of the apparatus of FIG. 1.

FIGS. 1 and 2 show a sterilizing apparatus designed in accordance with the invention. Bowl 1 holds a bed of porous particles 3 impregnated with liquid disinfectant. Only a portion of the bed of porous particles is shown in these figures, it being understood that the bed extends across the bottom 5 of the bowl. The bowl contains an opening 7 which permits insertion of a person's hand or other object to be sterilized.

Figure 3:
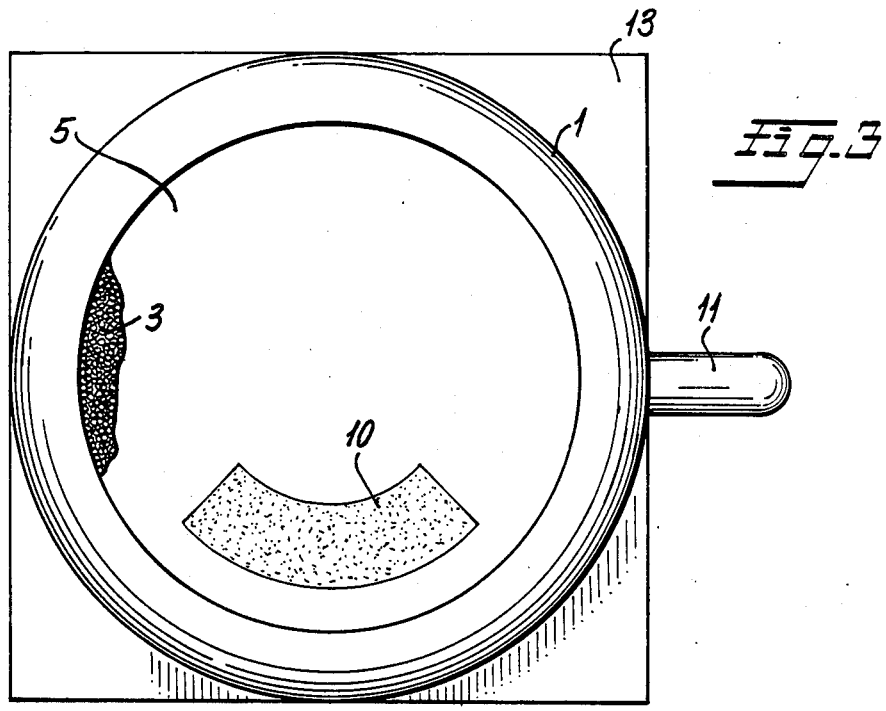
FIG. 3 shows a top view of an apparatus designed in accordance with the invention
Figure 4:
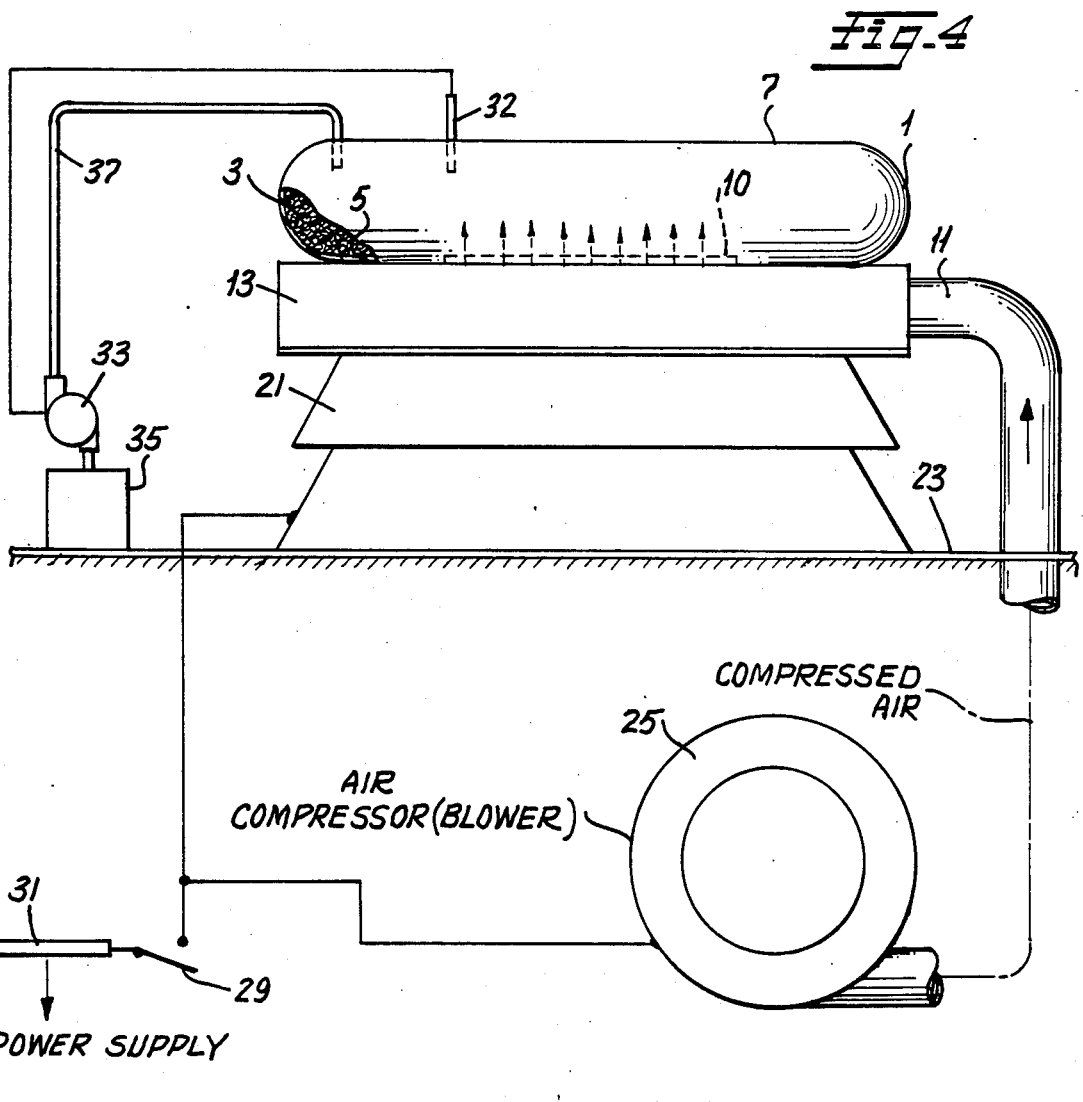
FIG. 4 shows a side view in partial cross section of the apparatus of FIG. 3.

In operation, the bowl is mechanically vibrated by vibrating table 9 which imparts vibrational forces to the bowl, causing particles 3 to become agitated within the bowl. The frequency and amplitude of the vibration may be varied to optimize the motion of the particles in the bowl. The vibrations may be induced by means of a rotating eccentric mass or reciprocating electromagnetic, pneumatic or hydraulic means, as is well known in the art. An example of such vibration inducing means is the Turbo Tumblers sold by Lyman Products. This device employs a rotating eccentric mass to generate vibrational forces which can be transferred to the bottom of the bowl through table 9 or by placing the bowl thereon, as shown in FIGS. 3 and 4 described hereinafter.

The shape of bowl 1 may be selected to accomodate a variety of objects to be sterilized. The only requirements are that it has a relatively flat surface for receiving the vibrational forces and an opening to permit introduction of objects to be sterilized.

As shown in FIGS. 1 and 2, the bed of particles 3 is further agitated utilizing fluidized bed techniques, such as those used in oil refining, handling dry powders, chemical reactors, etc. A piece of porous sheet material 10, preferably polyethylene ($\frac{1}{8}$" thick, 100 micron porosity), mechanically reinforced by wire screening is pressurized with air provided by a blower or compressor (not shown). Generally, pressures of 6 to 12 inches of water are sufficient. The air is introduced through inlet 11 into the plenum chamber 13 disposed beneath the bowl. In this manner, air is delivered to the bowl through the porous sheet material, imparting fluidizing forces to the porous particles in the bowl. The plenum chamber also serves to mechanically connect the bottom 5 of the bowl to the vibrating table 9 for transferring the vibrational forces thereto. The connection of the bowl 1, plenum chamber 13 and vibrating table 9 is done by conventional means, e.g., mechanical coupling.

When the bed of particles is subjected to simultaneous vibrational and fluidizing forces, it appears to be vigorously "boiling" with the particles moving in random motion in the bowl. It is this vigorous agitation of the particles which causes them to impinge upon an object inserted therein and release a micro-thin film of liquid disinfectant held within the pores of the particles. The impingement of the particles on the object also serves to "scrub" the object proving a further means of removing pathogens.

The particles which form the bed in bowl 1 are preferably small, spherical beads of silica gel, such as those sold under the trademark "Britesorb" by the PQ Corporation of Valley Forge, Pa. These beads have a particle diameter of from about 1 to 2 mm and have high adsorbency properties allowing them to hold a relatively large quantity of liquid disinfectant. Other materials which could be used as the particles in the invention include, adsorbent materials such as corn cobs, vermiculite, perlite, porous plastics, porous ceramics and porous rubber. In addition, abrasive particles, such as $Al_2O_3$, or other fine abrasives, may be added to the bed to provide mild abrasive scrubbing as well as sterilization.

The liquid disinfectant which is used in the invention may be any of a number of substances which are known to be effective against a wide range of pathogens. While liquid disinfectants employing stabilized chlorine dioxide ($ClO_2$) are preferred, other liquid disinfectants capable of killing pathogenic microorganisms, as well as non-pathogenic microorganisms, such as bacteria, viruses, fungi, yeast, protazoans and the like, can be used in the invention. However, preferred disinfectants are those which are known to kill pathogenic microorganisms. Active ingredients which are suitable for this purpose include halogens, especially chlorine and iodine, phenols, alkylphenols, alcohols, quaternary ammonium compounds, orthophenolphenol and combinations thereof. Various inert or non-active ingredients may be included such as surfactants, perfumes, thickening agents, skin softeners, etc. The liquid disinfectant is impregnated in the particles by simply pouring, spraying, or otherwise applying it to the bed. The particles adsorb the liquid disinfectant in their pores. Sufficient disinfectant should be applied to fully load the particles without providing an unadsorbed excess. Recharging the particles by reapplication of disinfectant must be performed periodically. Recharging may be accomplished automatically by providing a moisture sensing element in the bowl which is connected to a small pump and disinfectant reservoir which can be activated to supply disinfectant to the bowl when the moisture sensor readings fall below a predetermined level indicative of a low disinfectant level.

Referring to FIGS. 3 and 4, another embodiment of the invention is shown. To avoid repetition, like elements in these figures are provided with the same reference numerals as in FIGS. 1 and 2. In this embodiment, the vibrational forces are provided by vibrating mechanism 21 which is mechanically connected to plenum chamber 13, and supported by table 23. Air introduced into the plenum chamber is provided by blower 25 located underneath table 23 and connected to an inlet 11 by conduit 27. Both the blower 25 and vibrating mechanism 21 are energized by a power supply (not shown) which will typically be a standard electrical wall outlet. A switch 29, activated by foot pedal 31 controls the supply of power to the blower and vibrating mechanism. In an optional embodiment, the bowl 1 may be provided with a cover which is automatically opened when switch 29 is closed, permitting insertion of objects into the bowl at the same time that the particles therein are agitated by the application of the vibrational and fluidizing forces.

In operating the apparatus of the invention depicted in FIGS. 3 and 4, the foot pedal is depressed, closing switch 29 which energizes the vibrating mechanism 21 and blower 25 causing the particles 3 to violently move in random directions within bowl 1. Any covering on the bowl is then removed manually or automatically, and the object to be sterilized is immersed in the bed of agitated particles for at least about 10 and preferably 15 seconds. The sterilized object is then removed from the bowl as foot pedal 31 is released, opening switch 29 which shuts off the blower and vibrator and, optionally, closes the cover of the bowl.

Also shown in FIG. 4, is means for automatically replenishing the liquid disinfectant. Moisture sensor 31 senses the level of liquid disinfectant available on the surface of the particles. When this level falls below a predetermined minimum, the sensor energizes the pump 33 which pumps disinfectant from storage reservoir conduit 37 and into bowl 1, where it is adsorbed by the particles.

The method and apparatus of the invention thus provides a convenient, simple and effective means for sterilizing objects, particularly human hands, gloved or uncovered. Although the invention has been described using the combination of vibrational and fluidizing forces to agitate the particle bed, it should be understood that other means could be employed to agitate, such as sandblasting, shotblasting, vibration alone, fluidizing alone or combinations of these techniques.

The method and apparatus of the invention may also be used to sterilize a variety of objects, in addition to hands, including but not limited to medical and dental instruments, feet in shower rooms, shoe covers in operating rooms, etc.

Accordingly, it is understood that while the invention has been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

What is claimed is:

1. A method of sterilizing an object comprising immersing the object in an agitated bed of porous particles impregnated with a liquid disinfectant such that the particles strike a surface of the object immersed therein and release a micro-thin film of the liquid disinfectant onto the surface of the object, thereby killing pathogens on said surface of the object.

2. The method of claim 1, wherein said object is a human hand.

3. The method of claim 1, wherein said porous particles are spherical beads of silica gel.

4. The method of claim 1, wherein said porous particles are in random motion within said agitated bed.

5. The method of claim 1, wherein said object is immersed in said agitated bed for at least about 10 seconds.

6. The method of claim 1, wherein said agitated bed is agitated by vibrational and fluidizing forces.

* * * * *